(12) United States Patent
Flight

(10) Patent No.: US 11,534,189 B2
(45) Date of Patent: Dec. 27, 2022

(54) SURGICAL BASKET

(71) Applicant: Gyrus ACMI, Inc., Southborough, MA (US)

(72) Inventor: Bruce W. Flight, Melrose, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 18 days.

(21) Appl. No.: 16/290,231

(22) Filed: Mar. 1, 2019

(65) Prior Publication Data

US 2020/0275941 A1    Sep. 3, 2020

(51) Int. Cl.
 *A61B 17/221* (2006.01)
 *A61B 17/00* (2006.01)
 *A61B 17/3205* (2006.01)

(52) U.S. Cl.
 CPC ...... *A61B 17/221* (2013.01); *A61B 17/00234* (2013.01); *A61B 17/32056* (2013.01); *A61B 2017/00526* (2013.01); *A61B 2017/2212* (2013.01); *A61B 2017/2215* (2013.01)

(58) Field of Classification Search
 CPC ............ A61B 17/221; A61B 17/00234; A61B 17/32056; A61B 2017/00526; A61B 2017/2212; A61B 2017/2215; A61B 2017/2217
 See application file for complete search history.

(56) References Cited

U.S. PATENT DOCUMENTS

| | | | |
|---|---|---|---|
| 5,944,728 A | 8/1999 | Bates | |
| 6,099,534 A | 8/2000 | Bates et al. | |
| 6,764,499 B2 | 7/2004 | Honey et al. | |
| 8,211,115 B2 | 7/2012 | Cheng et al. | |
| 9,039,715 B2 | 5/2015 | Diamant et al. | |
| 9,168,099 B2 | 10/2015 | St. George | |
| 9,936,967 B2 | 4/2018 | Galperin et al. | |
| 2013/0261638 A1* | 10/2013 | Diamant | A61M 1/0023 606/113 |
| 2015/0142009 A1 | 5/2015 | Ahn | |
| 2016/0242795 A1 | 8/2016 | Iwabuchi et al. | |
| 2016/0256179 A1* | 9/2016 | Walish | A61M 25/0074 |

(Continued)

FOREIGN PATENT DOCUMENTS

| | | |
|---|---|---|
| CN | 109247971 A | 1/2019 |
| CN | 111631780 A | 9/2020 |
| EP | 1182975 A2 | 3/2002 |

(Continued)

OTHER PUBLICATIONS

"European Application Serial No. 20159414.0, Extended European Search Report dated Jun. 29, 2020", 7 pgs.

(Continued)

*Primary Examiner* — Martin T Ton
(74) *Attorney, Agent, or Firm* — Schwegman Lundberg & Woessner, P.A.

(57) ABSTRACT

An apparatus including a basket device including a basket section; and a sheath on the basket device. The basket device and the sheath are configured to longitudinally slide relative to each other. The basket section includes at least two groups of loop petals including a first group having at least two first loop petals and a second group having at least two second loop petals, where the first loop petals have a different size than the second loop petals.

14 Claims, 5 Drawing Sheets

(56) References Cited

U.S. PATENT DOCUMENTS

2017/0296219 A1    10/2017    Avneri et al.

FOREIGN PATENT DOCUMENTS

| EP | 1408854 A1 | | 4/2004 |
|---|---|---|---|
| EP | 3701887 A1 | | 9/2020 |
| JP | 2016030077 A | * | 3/2016 |
| JP | 2020138027 A | | 9/2020 |
| WO | WO-02/39912 A1 | | 5/2002 |
| WO | WO-2015072394 A1 | | 5/2015 |
| WO | WO-2017-153810 A1 | | 9/2017 |
| WO | WO-2017/199066 A1 | | 11/2017 |

OTHER PUBLICATIONS

"European Application Serial No. 20159414.0, Response filed Mar. 2, 2021 to Extended European Search Report dated Jun. 29, 2020", 11 pgs.

"Japanese Application Serial No. 2020-33846, Notification of Reasons for Refusal dated Feb. 8, 2021", w/ English Translation, 9 pgs.

"Japanese Application Serial No. 2020-33846, Response filed May 10, 2021 to Notification of Reasons for Refusal dated Feb. 8, 2021", w/ English Claims, 12 pgs.

"Japanese Application Serial No. 2020-33846, Examiners Decision of Final Refusal dated Sep. 21, 2021", w/ English Translation, 9 pgs.

"European Application Serial No. 20159414.0, Communication Pursuant to Article 94(3) EPC dated May 18, 2022", 6 pgs.

"Japanese Application Serial No. 2020-33846, Preliminary Examination Report dated Apr. 11, 2022", w/ English Translation, 2 pgs.

"Japanese Application Serial No. 2020-33846, Response filed Jan. 21, 2022 to Examiners Decision of Final Refusal dated Sep. 21, 2021", w/ English Claims, 20 pgs.

"Japanese Application Serial No. 2020-33846, Response filed Jul. 11, 2022 to Preliminary Examination Report dated Apr. 11, 2022", w English claims, 5 pgs.

"European Application Serial No. 20159414.0, Communication Pursuant to Article 94(3) EPC dated May 18, 2022", 10 pgs.

"Japanese Application Serial No. 2020-33846, Notification of Reasons for Refusal dated Oct. 3, 2022", w/ English translation, 10 pgs.

* cited by examiner

SURGICAL BASKET

BACKGROUND

Technical Field

The example and non-limiting embodiments relate generally to a device having a basket and, more particularly, to a method and apparatus for a closable basket.

BRIEF DESCRIPTION OF PRIOR DEVELOPMENTS

U.S. Pat. No. 6,764,499 discloses a medical device with a basket. U.S. Pat. No. 8,211,115 discloses a variable size retrieval basket.

SUMMARY

The following summary is merely intended to be exemplary. The summary is not intended to limit the scope of the claims.

In accordance with one aspect, an example embodiment may be provided in an apparatus comprising a basket device comprising a basket section; and a sheath on the basket device, where the basket device and the sheath are configured to longitudinally slide relative to each other, where the basket section comprises at least two groups of loop petals comprising a first group including at least two first loop petals and a second group including at least two second loop petals, where the first loop petals have a different size than the second loop petals.

In accordance with another aspect, an example embodiment may be provided in an apparatus comprising: a basket device comprising a basket section; and a sheath on the basket device, where the basket device and the sheath are configured to longitudinally slide relative to each other, where the basket section comprises at least two groups of petals comprising a first group of petals and a second group of petals, where the first group of petals are sized and shaped to be moved at a different rate than the second group of petals by the sheath as the basket device and the sheath are longitudinally slid relative to each other.

In accordance with another aspect, an example method may be provided comprising: providing a basket device comprising a basket section, where the basket section comprises at least two groups of loop petals comprising a first group including at least two first loop petals and a second group including at least two second loop petals, where the first loop petals have a different size than the second loop petals; and connecting a sheath to the basket device, where the basket device and the sheath are configured to longitudinally slide relative to each other, and where the first group of petals are sized and shaped to be moved by the sheath at a different rate than the second group of petals as the basket device and the sheath are longitudinally slid relative to each other.

In accordance with another aspect, an example method may be provided comprising: longitudinally sliding a sheath and a basket device relative to each other, where the basket device comprising a basket section, where the basket section comprises at least two groups of petals comprising a first group including at least two first petals and a second group including at least two second petals, and where the first petals have a different size than the second petals; moving the first group of petals by the sheath at a first rate as the basket device and the sheath are longitudinally slid relative to each other; and moving the second group of petals by the sheath at a different second rate as the basket device and the sheath are longitudinally slid relative to each other.

BRIEF DESCRIPTION OF THE DRAWINGS

The foregoing aspects and other features are explained in the following description, taken in connection with the accompanying drawings, wherein.

DETAILED DESCRIPTION OF EMBODIMENTS

Figure 1:
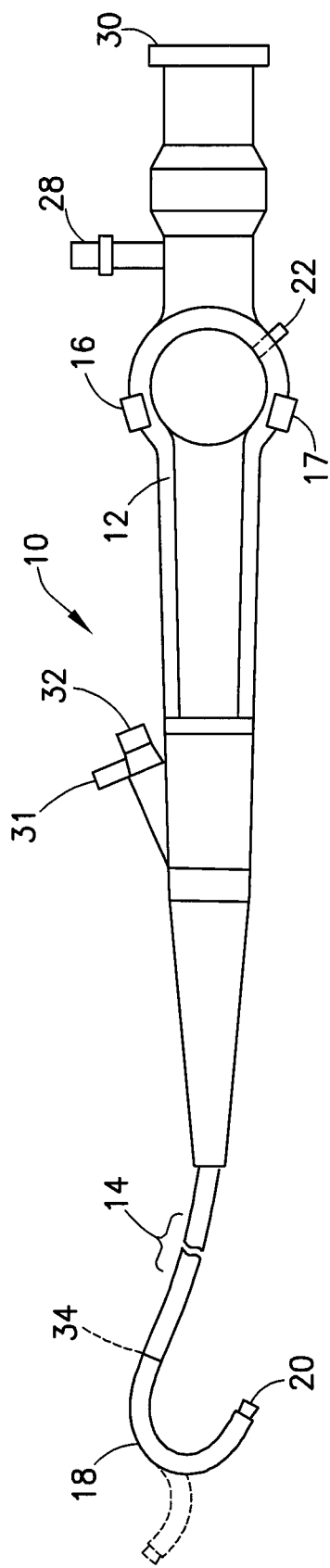
FIG. 1 is a schematic side view of an endoscope.

Referring to FIG. 1, there is shown a side elevational view of an endoscope 10 incorporating features of the present invention. Although the present invention will be described with reference to the embodiments shown in the drawings, it should be understood that the present invention can be embodied in many alternate forms of embodiments. In addition, any suitable size, shape or type of elements or materials could be used.

The endoscope 10, in this embodiment, is a flexible ureteropyeloscope. The endoscope 10 generally comprises a handle 12, a flexible shaft 14 connected to the handle 12, and a distal end 18 of the shaft which has an active deflection capability. Please note that this is merely one example of an endoscope. Features as described herein may be used with any suitable type of endoscope having a working channel.

The handle 12 is part of a control system to control the active deflection capability of the distal end 18. The control system generally comprises the handle 12, two actuators 16, 17, a brake actuator 22, and three control wires (not shown). However, in alternate embodiments, the control system could comprise additional or alternative components. The three actuators 16, 17, 22 are movably attached to the handle 12. Proximal ends of the wires are connected to the two control actuators 16, 17. The brake actuator 22 is connected to a braking mechanism for locking the second control actuator 17 at a fixed position. However, in an alternate embodiment, any suitable type of brake or locking mechanism could be provided. In one type of alternate embodiment, the endoscope might not comprise a control actuator brake. In the embodiment shown, the first control actuator 16 does not comprise a brake.

The handle 12 also comprises a light source post 28, an eyepiece 30, irrigation inlet 31 and working instrument inlet 32. However, in alternate embodiments, the handle 12 could comprise additional or alternative components. A working channel 34 extends through the handle 12 and the shaft 14 between the inlet 32 and an outlet at the distal end 20. The endoscope 10 includes a fiber-optic illumination bundle which extends through the shaft 14 between the light post 28 and the distal end 20. A fiber optic image bundle extends through the shaft 14 between the eyepiece 30 and the distal end 20.

Figure 2:
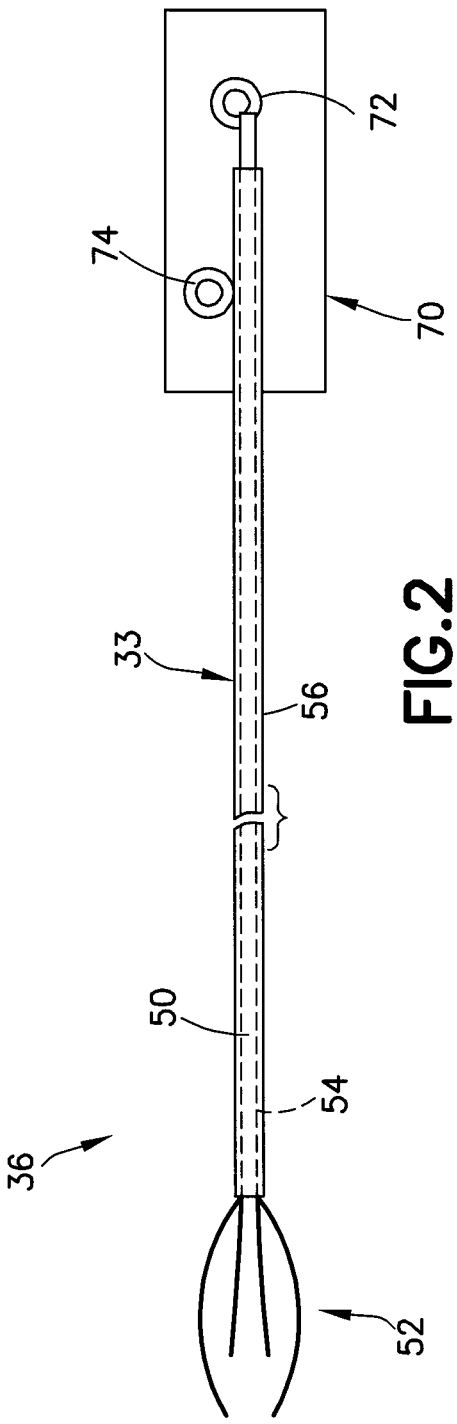
FIG. 2 is a schematic side view of an example apparatus comprising features as described herein.

Referring also to FIG. 2, a schematic side view of a medical device or tool 36 for use with the endoscope 10 is shown. It should be noted that the terms "side" and "top" as used herein are merely examples used for clarity. The apparatus 36 and basket section 52 may have any suitable orientation while inside the patient. The tool 36 is configured to be attached to the endoscope 10 and is configured to extend out of the distal end 20 of the shaft 14 from the working channel 34. The tool 36, in this example, is a Surgeon Controlled Basket Device (SCBD). The tool 36 includes an assembly 33 which comprises a basket device 50 and a sheath 56. The basket device 50 comprises a basket section 52 at a distal end, and a shaft section 54 extending through the sheath 56 to a proximal end of the tool 36. The sheath 56 and basket device 50 are longitudinally movable relative to each other to move the sheath 56 between a forward position and a rearward position relative to the basket device 50.

When the sheath 56 is at its forward position relative to the basket device 50, the basket section 52 is located inside the sheath 56, and the basket section 52 is collapsed by the sheath 56 into a smaller shape to fit inside the sheath 56. This relative position of the basket section 52 inside the sheath 56 is used to insert the tool 36 into the inlet 32 of the endoscope 10 and through the working channel 34.

Figure 3:
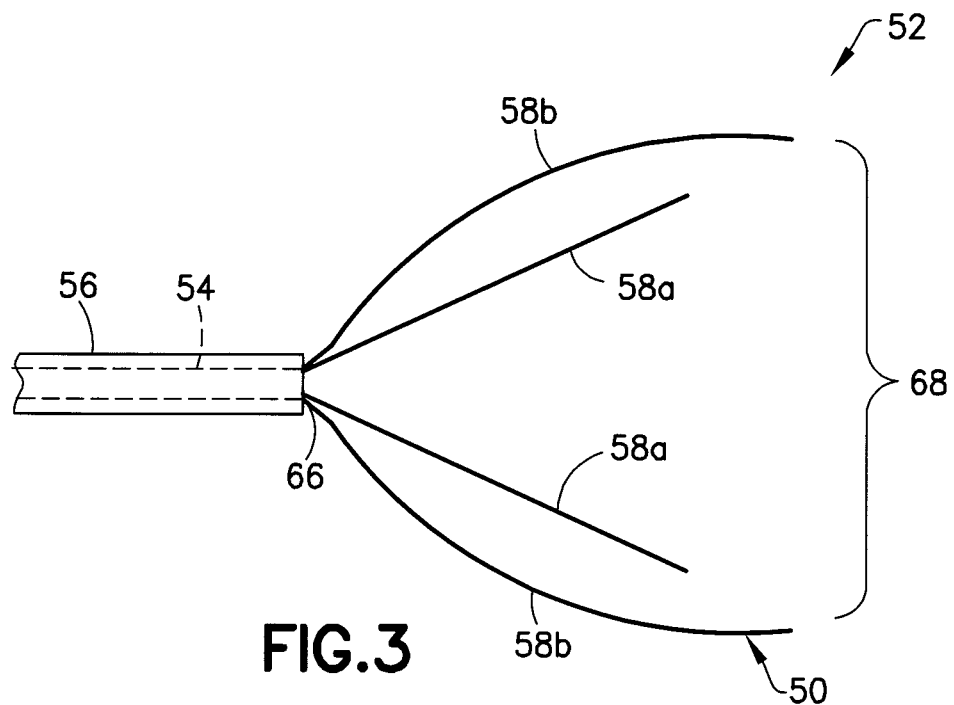
FIG. 3 is an enlarged side view of the distal end of the apparatus shown in FIG. 2.
Figure 4:
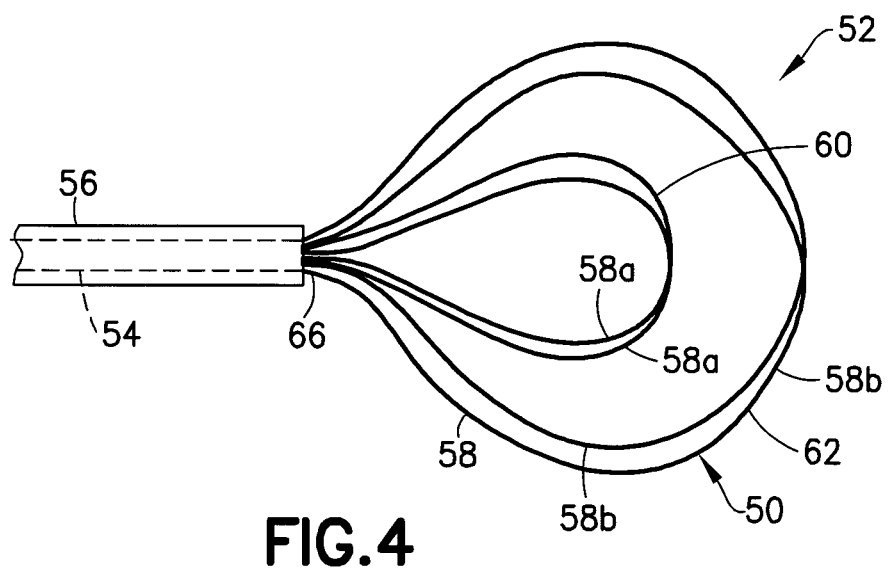
FIG. 4 is a top view of the distal end of the apparatus as shown in FIG. 3.

Referring also to FIGS. 3 and 4, these figures show the sheath 56 at its rearward position relative to the basket device 50. The basket section 52 extends out from a front end aperture 66 of the sheath 56. As the basket section 52 is exposed out of the front end aperture 66, the basket section 52 resiliently expands into the shape shown.

As seen in FIG. 2, the proximal end of the tool 36 comprises a controller 70. The assembly 33 may be removably connected to the controller 70. The controller 70 is intended to remain outside of the working channel 24 to allow the user to operate the tool 36. The controller 70 generally comprises a first section 72 and a second section 74. The proximal end of the shaft section 54 is fixedly connected to the first section 72 such that the proximal end of the shaft section 54 does not move relative to the controller 70. The proximal end of the sheath 56 is connected to the second section 74. The second section 74 is configured to longitudinally move the sheath 56 relative to the shaft section 54. Thus, the sheath 56 can be in a forward position to cover the basket section 52, or can be in a rearward position to allow the basket section 52 to be uncovered. In alternate example embodiments, any suitable type of controller for moving the sheath 56 and the basket device 50 relative to each other could be provided. The controller 70 is also configured to longitudinally move the basket device and the sheath relative to each other to close the basket section on an object.

Referring particularly to FIGS. 3-4, the basket section 52 in this example comprises petals 58 which extend from the distal end of the shaft section 54. The petals 58 may be formed from Nitinol wire, or other shape memory alloy, or a combination of shape memory materials for example. Each of the petals 58 has a general loop shape extending from the shaft section 54. However, other shapes could be provided.

In this example embodiment the petals 58 comprise a first group 60 of the petals and a second group 62 of the petals. In alternate example embodiments, more than two groups of petals could be provided. The first group 60 of petals comprises two first petals 58a. The second group 62 of petals comprises two second petals 58b. However, in alternate example embodiments more than two first petals and more than two second petals could be provided. The first petals 58a have a different size and shape than the second petals 58b. More specifically, the first petals 58a are smaller than the second petals 58b, and the first petals 58a have a substantially straight side profile (as seen best in FIG. 3) versus a relatively curved profile of the second petals 58b. As seen best in FIG. 3, each of the first petals 58a are located at a same side of the basket section as a respective one of the second petals 58b. As further understood below, the first group 60 of petals are sized and shaped to be moved at a different rate than the second group 62 of petals by the sheath 56 as the basket device and the sheath are longitudinally slid relative to each other. It should be noted that this is merely an example of the first and second petals and the first and second groups. Other sizes, shapes and relative configurations could be provided.

Figure 5:
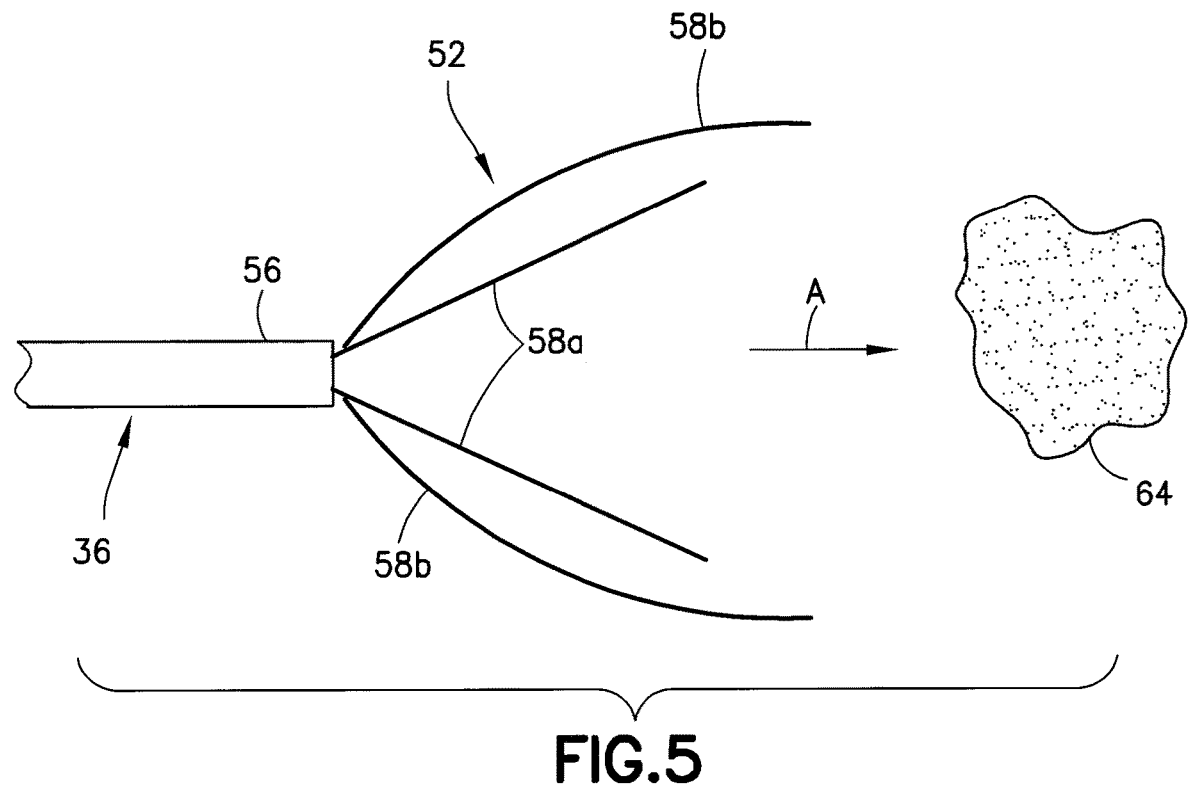
FIG. 5 is a side view of the distal end of the apparatus shown in FIG. 3 which is shown moving towards an object to be grasped.
Figure 6:
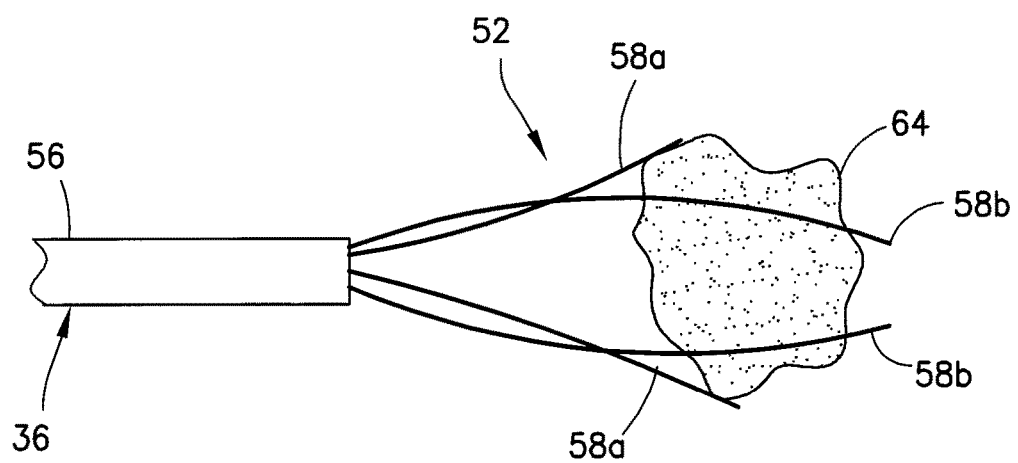
FIG. 6 is a side view as in FIG. 5 showing the object having been grasped by the apparatus.
Figure 7:
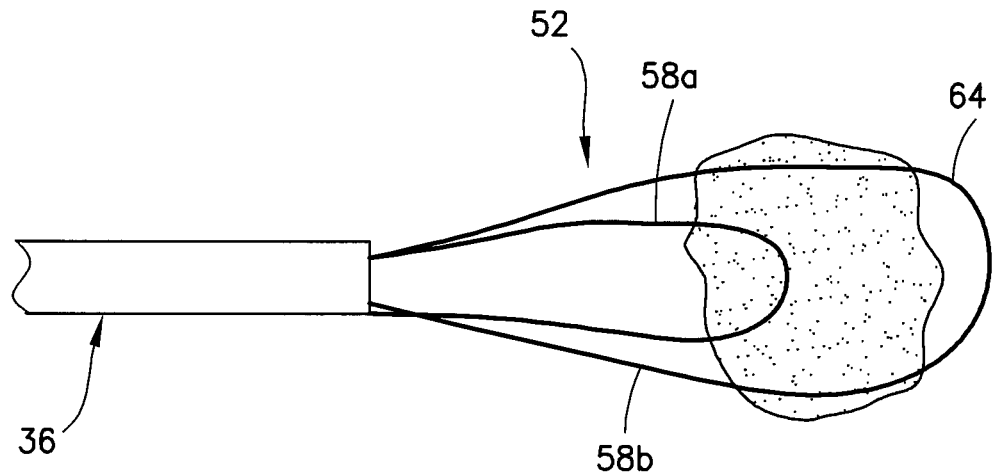
FIG. 7 is a top view of the apparatus and object as shown in FIG. 6.

After the basket section 52 has been deployed relative to the sheath 56 as shown in FIGS. 3-4, the sheath 56 may be moved forward to partially move rear portions of the petals 58 back into the sheath 56. This causes a collapsing motion of the basket section 52. This collapsing motion may be used to cause the basket section 52 to come into contact with an object as the sheath is longitudinally slid on the basket device. This is shown in FIGS. 5-7 for example. As shown in these figures, an object 64, such as a kidney stone for example, may be located and the tool 36 is then moved into position as shown by arrow A. The tool is then used to grab the object 64 (FIGS. 6-7) for subsequent removal or further action on the object 64. More specifically, the deployed basket section 52 is moved to a position where the object is located between opposing petals 58, and then sheath 56 is then moved forward on the basket device 50 to deflect the opposing petals 58 towards one another and clamp the object 64 therebetween. In this example, the petals 58 are arranged to provide the basket section 52 with a substantially open front end 68 as shown best in FIG. 3. This helps to allow a larger stone 64 to enter between the larger petals 58b before the petals 58b are closed onto the stone.

Figure 9:
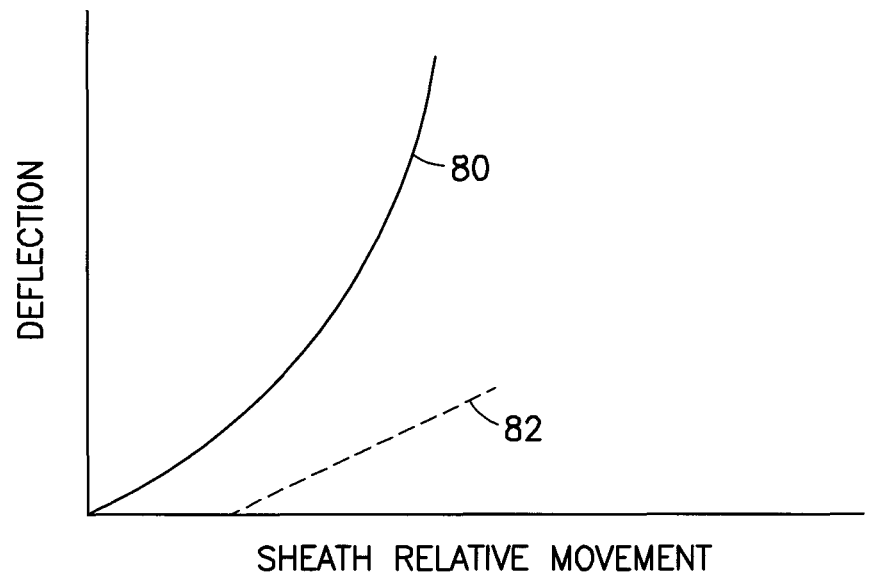
FIG. 9 is a diagram illustrating the different rates of movement of distal tips of the two different types of petals.
Figure 10:
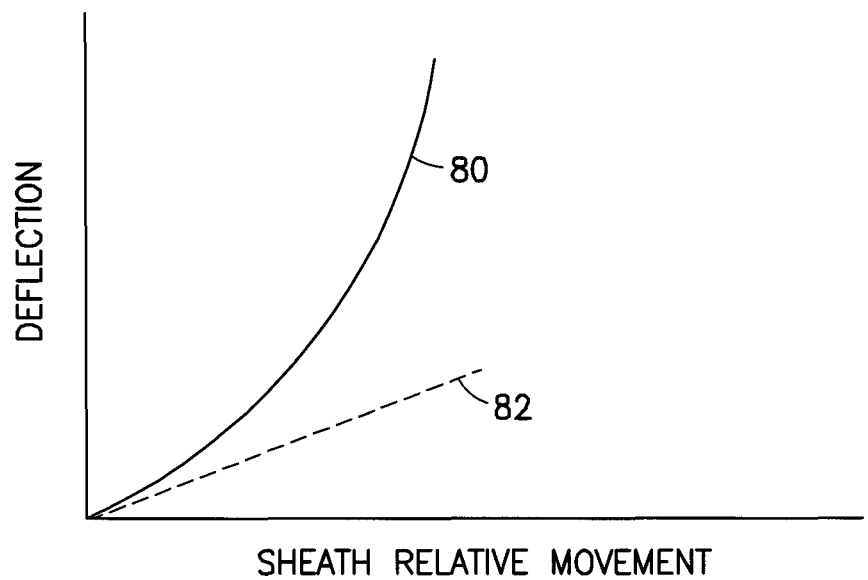
FIG. 10 is a diagram as in FIG. 9 of an alternate example embodiment.

In this particular example the second group 62 of petals is configured to contact the object 64 before the first group 60 of petals contacts the object 64. More specifically, as the basket device 50 and the sheath 56 are longitudinally slid relative to each other, the second petals 58b are sized and shaped relative to the first petals 58a such that contact between the rear ends of the petals 58a, 58b and the sheath 56 starts to move the second petals 58b towards each other before the first petals 58a start to move towards each other. In addition, the size and shape of the second petals 58b relative to the first petals 58a causes the second petals 58b to move towards each other faster than the first petals 58a move towards each other. Thus, in this example, the rates of movement are different both in regard to start times of inward deflection and in regard to speed of inwards deflection. In alternate examples, the start times might be the same and the relative speed different, or the relative speeds might be the same and the start times might be different. The different rates of the collapsing motion of the first group 60 of petals and the second group 62 of petals, including when collapsing starts, may all be configured based upon the different size and/or shape of the first petals relative to the second petals. Referring also to FIG. 9, a schematic diagram illustrating the different rates in this example are shown. As the sheath 56 is moved forward on the basket device 50 the larger petals 58b are deflected as indicated by line 80 and then the smaller petals 58a are subsequently deflected as indicated by line 82. The deflection 80 has a curved profile and the deflection 82 has a straight profile. However, in alternate embodiments this could be different. Referring also to FIG. 10 another example is shown where both deflections start at substantially a same time, but the rates of deflection are still different. This are merely examples for illustration of the different rate differential concept.

The distal end of the deployed capture device may be advanced over the stone 64 such that the larger outer petals 58b of the capture device extend to the distal-most position of the stone 64. As the outer sheath is advanced to close the capture device, the larger outer petals 58b may surround and capture the distal-most end of the stone 64 while the smaller inner petals 58a close inward to secure the stone at opposing sides within the capture device. If required, the captured stone 64 may be released from the basket section 52 for re-positioning by retracting the outer sheath to re-open the basket section 52 to its original fully deployed shape.

Figure 8:
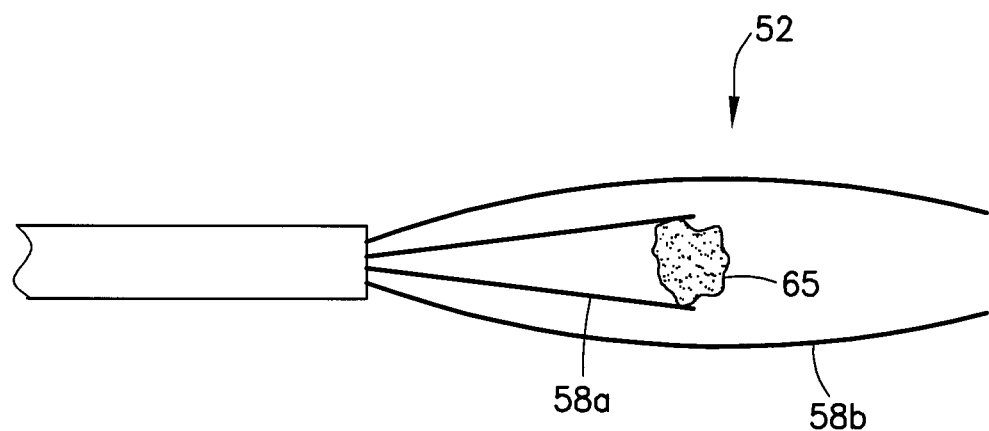
FIG. 8 is a side view as in FIG. 6 showing the basket section grasping a smaller stone.

With features as described herein, a distal capture device may be provide which is able to capture and retain stones of a broad range of sizes for removal or, for larger stones, to be able to capture, retain and release to reposition in a more desirable location; such as for fragmentation into smaller particles and subsequent removal. Conventional basket designs may have difficulty retaining smaller stones due to larger open areas within a partially closed basket. Further, conventional distal capture devices with multiple tubular capture legs connected together at their distal extremities may have difficulty releasing large stones. Features as described herein may comprise using a shorter inner petals to improve the ability to retain smaller captured stones for removal, but nonetheless also retain larger stones. Thus, the basket section 52 has a greater range of stone sizes which it can be used efficiently. This is illustrated with reference to FIG. 8 which shows the basket section 52 grasping a smaller stone 65. In this example the smaller stone 65 is merely grasped by the smaller petals 58a without any grasping contact by the larger petals 58b.

With features as described herein, providing a second progressively actuated gripping petal, such as first petals 58a, within a primary distal-most stone capture petal, such as second petals 58b, allows for improved stone retention within the partially closed basket section. The example described above will also allow for a progressive petal action upon opening of the basket section to allow for a more controlled release of a larger stone for repositioning and improved ability to retain smaller stones for removal.

A difference with a device comprising features as described herein versus a conventional device is the progressive motion (closure/opening) action to first capture (via the second petals 58b) a stone and then subsequently secure (via both the second petals 58b and the first petals 58a) the stone within the basket section for removal of the stone, or for repositioning of a larger stone to be fractured into smaller and more easily removable fragments. This type of stone retrieval device with distal end capture capability may be used, for example, when retrieving a stone typically within a lower pole of the kidney and against the kidney wall where a traditional side capture stone retrieval basket would be required to extend distally past the stone to facilitate stone entrance into the basket. The design of this device, with the addition of inner petals 58a, improves the ability to retain smaller captured stones for removal, whereas a convention distal capture grasper type device would have difficulty retaining a captured stone and their typical single-wire grasping legs have a greater potential to cause injury to the patient. With features as described herein, there is a lesser potential to cause injury to the patient than a conventional device.

In accordance with one example embodiment, a medical device or tool may be provided comprising: a sheath having a proximal end, a distal end and, a hollow passageway within the sheath that extends from the proximal to the distal end; at least four opposing legs having a collapsed position in which the legs are collapsed within the lumen of the sheath and another position in which the legs extend from the distal end of the sheath and out of the lumen, the legs being moveable between an open position and a closed position with the legs being closer together at their distal ends when in the closed position than when in the open position to allow capture and release of material, at least two of the legs having a different length from the base to its distal end than at least one other of the legs.

An example embodiment may be provided in an apparatus comprising a basket device comprising a basket section; and a sheath on the basket device, where the basket device and the sheath are configured to longitudinally slide relative to each other, where the basket section comprises at least two groups of loop petals comprising a first group including at least two first loop petals and a second group including at least two second loop petals, where the first loop petals have a different size than the second loop petals.

The apparatus may further comprise a control connected to the basket device and the sheath, where the control is configured to longitudinally move the basket device and the sheath relative to each other to close the basket section on an object. The first group of loop petals may be sized and shaped to be moved at a different rate than the second group of loop petals by the sheath as the basket device and the sheath are longitudinally slid relative to each other. The basket section may be sized and shaped such that as the basket device and the sheath are longitudinally slid relative to each other, contact between the basket section and the sheath is configured to start to move the at least two second loop petals towards each other before the contact between the basket section and the sheath causes at least two first loop petals to start to move the towards each other. The first loop petals may have a substantially straight profile, and where the second loop petals have a curved profile. The first group of loop petals and the second group of loop petals may be configured to be moved onto contact with an object as the sheath is longitudinally slid on the basket device, and where the second group of loop petals is configured to contact the object before the first group of loop petals contact the object. The first loop petals may be smaller than the second loop petals. Each of the first loop petals may be located at a same side of the basket section as a respective one of the second loop petals.

An example embodiment may be provided in an apparatus comprising a basket device comprising a basket section; and a sheath on the basket device, where the basket device and the sheath are configured to longitudinally slide relative to each other, where the basket section comprises at least two groups of petals comprising a first group of petals and a second group of petals, where the first group of petals are sized and shaped to be moved at a different rate than the second group of petals by the sheath as the basket device and the sheath are longitudinally slid relative to each other.

The apparatus may further comprise a control connected to the basket device and the sheath, where the control is configured to longitudinally move the basket device and the sheath relative to each other to close the basket section on an object. The basket section may be sized and shaped such that as the basket device and the sheath are longitudinally slid relative to each other, contact between the basket section and the sheath is configured to start to move the at least two second petals towards each other before the contact between the basket section and the sheath causes at least two first petals to start to move the towards each other. The first petals may have a substantially straight profile, and where the second petals have a curved profile. The first group of petals and the second group of petals may be configured to be moved onto contact with an object as the sheath is longitudinally slid on the basket device, and where the second group of petals is configured to contact the object before the first group of petals contact the object. The first petals may be smaller than the second petals. Each of the first petals may be located at a same side of the basket section as a respective one of the second petals.

An example method may be provided comprising providing a basket device comprising a basket section, where the basket section comprises at least two groups of loop petals comprising a first group including at least two first loop petals and a second group including at least two second loop petals, where the first loop petals have a different size than the second loop petals; and connecting a sheath to the basket device, where the basket device and the sheath are configured to longitudinally slide relative to each other, and where the first group of petals are sized and shaped to be moved by the sheath at a different rate than the second group of petals as the basket device and the sheath are longitudinally slid relative to each other.

The method may further comprise connecting a control to the basket device and the sheath, where the control is configured to longitudinally move the basket device and the sheath relative to each other to close the basket section on an object. Providing the basket device may comprise the basket section being sized and shaped such that as the basket device and the sheath are longitudinally slid relative to each other, contact between the basket section and the sheath is configured to start to move the at least two second loop petals towards each other before the contact between the basket section and the sheath causes at least two first loop petals to start to move the towards each other. Providing the basket device may comprise the first loop petals having a substantially straight profile, the second loop petals having a curved profile, and where first loop petals are smaller than the second loop petals. Providing the basket device may comprise the first group of loop petals and the second group of loop petals being configured to be moved onto contact with an object as the sheath is longitudinally slid on the basket device, and where the second group of loop petals is configured to contact the object before the first group of loop petals contact the object. Providing the basket device may comprise each of the first loop petals being located at a same side of the basket section as a respective one of the second loop petals.

An example method may be provided comprising longitudinally sliding a sheath and a basket device relative to each other, where the basket device comprising a basket section, where the basket section comprises at least two groups of petals comprising a first group including at least two first petals and a second group including at least two second petals, and where the first petals have a different size than the second petals; moving the first group of petals by the sheath at a first rate as the basket device and the sheath are longitudinally slid relative to each other; and moving the second group of petals by the sheath at a different second rate as the basket device and the sheath are longitudinally slid relative to each other.

Moving the second group of petals by the sheath at a different second rate may cause at least one of: at least a portion of the second group of petals moving faster than the first group of petals, or a start to a move of the at least two second petals towards each other occurring before a start to a move of the at least two first petals towards each other, or the second group of petals contacting an object therebetween before the first group of petals contact the object therebetween.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. An apparatus comprising:
   a basket device comprising a basket section movable between a collapsed configuration and a deployed configuration; and
   a sheath on the basket device,
   where the basket device and the sheath are configured to longitudinally slide relative to each other,
   where the basket section comprises at least two groups of loop petals comprising a first group including at least two first loop petals and a second group including at least two second loop petals, where the first loop petals have a different size than the second loop petals,
   where in the deployed configuration, the first group of loop petals extends longitudinally beyond a distal end of the sheath by a first distance and the second group of loop petals extends longitudinally beyond the distal end of the sheath by a different second distance, and distal ends of the first loop petals are free from connection with distal ends of the second loop petals, and
   where the basket section is sized and shaped such that as the basket device and the sheath are longitudinally slid relative to each other, contact between the basket section and the sheath is configured to start to move the at least two second loop petals towards each other before the contact between the basket section and the sheath causes the at least two first loop petals to start to move towards each other, and wherein the first loop petals have a substantially straight profile, and where the second loop petals have a curved profile.

2. An apparatus as in claim 1 further comprising a control connected to the basket device and the sheath, where the control is configured to longitudinally move the basket device and the sheath relative to each other to close the basket section on an object.

3. An apparatus as in claim 1 where the first group of loop petals are sized and shaped to be moved at a different rate than the second group of loop petals by the sheath as the basket device and the sheath are longitudinally slid relative to each other.

4. An apparatus as in claim 1 where the first group of loop petals and the second group of loop petals are configured to be moved into contact with an object as the sheath is longitudinally slid on the basket device, and where the second group of loop petals is configured to contact the object before the first group of loop petals contact the object.

5. An apparatus as in claim 4 where first loop petals are smaller than the second loop petals.

6. An apparatus as in claim 1 where each of the first loop petals are located at a same side of the basket section as a respective one of the second loop petals.

7. An apparatus comprising:
   a basket device comprising a basket section movable between a collapsed configuration and a deployed configuration; and
   a sheath on the basket device,
   where the basket device and the sheath are configured to longitudinally slide relative to each other,
   where the basket section comprises at least two groups of petals comprising a first group of petals and a second group of petals, where the first group of petals are sized and shaped to be moved at a different rate than the second group of petals by the sheath as the basket device and the sheath are longitudinally slid relative to each other,
   where in the deployed configuration, the first group of petals extends longitudinally beyond a distal end of the sheath by a first distance and the second group of petals extends longitudinally beyond the distal end of the sheath by a different second distance such that distal ends of the first group of petals remain physically separated from distal ends of the second group of petals and such that the distal ends of the first group of petals are free from connection with the distal ends of the second group of petals,
   where the basket section is sized and shaped such that as the basket device and the sheath are longitudinally slid relative to each other contact between the basket section and the sheath is configured to start to move the second group of petals towards each other before the contact between the basket section and the sheath causes the first group of petals to start to move towards each other, and wherein the first petals have a substantially straight profile, and where the second petals have a curved profile.

8. An apparatus as in claim 7 further comprising a control connected to the basket device and the sheath, where the control is configured to longitudinally move the basket device and the sheath relative to each other to close the basket section on an object.

9. An apparatus as in claim 7 where the first group of petals and the second group of petals are configured to be moved Minto contact with an object as the sheath is longitudinally slid on the basket device, and where the second group of petals is configured to contact the object before the first group of petals contact the object.

10. An apparatus as in claim 9 where first petals are smaller than the second petals.

11. An apparatus as in claim 7 where each of the first petals are located at a same side of the basket section as a respective one of the second petals.

12. A method comprising:
   providing or obtaining a basket device comprising a basket section movable: between a collapsed configuration and a deployed configuration, where the basket section comprises at least two groups of loop petals comprising a first group including at least two first loop petals and a second group including at least two second loop petals, where the first loop petals have a different size than the second loop petals;
   connecting a sheath to the basket device, where the basket device and the sheath are configured to longitudinally slide relative to each other, where the first group of loop petals are sized and shaped to be moved by the sheath at a different rate than the second group of loop petals as the basket device and the sheath are longitudinally slid relative to each other, and where in the deployed configuration, the first group of loop petals extends longitudinally beyond a distal end of the sheath by a first distance and the second group of loop petals extends longitudinally beyond the distal end of the sheath by a different second distance, and distal ends of the first loop petals are free from connection with distal ends of the second loop petals;
   where providing the basket device comprises the basket section being sized and shaped such that as the basket device and the sheath are longitudinally slid relative to each other, contact between the basket section and the sheath is configured to start to move the at least two second loop petals towards each other before the contact between the basket section and the sheath causes the at least two first loop petals to start to move towards each other, and wherein providing the basket device comprises the first loop petals having a substantially straight profile, and the second loop petals having a curved profile, and where the first loop petals are smaller than the second loop petals.

13. A method as in claim 12 further comprising connecting a control to the basket device and the sheath, where the control is configured to longitudinally move the basket device and the sheath relative to each other to close the basket section on an object.

14. A method as in claim 12 where providing the basket device comprises the first group of loop petals and the second group of loop petals being configured to be moved into contact with an object as the sheath is longitudinally slid on the basket device, and where the second group of loop petals is configured to contact the object before the first group of loop petals contact the object.

* * * * *

UNITED STATES PATENT AND TRADEMARK OFFICE
CERTIFICATE OF CORRECTION

PATENT NO. : 11,534,189 B2
APPLICATION NO. : 16/290231
DATED : December 27, 2022
INVENTOR(S) : Bruce W. Flight Page 1 of 1

It is certified that error appears in the above-identified patent and that said Letters Patent is hereby corrected as shown below:

In the Claims

In Column 8, Line 44, in Claim 1, after "petals,", delete "and"

In Column 9, Line 35, in Claim 7, delete "other" and insert --other,-- therefor

In Column 9, Line 50, in Claim 9, delete "Minto" and insert --into-- therefor

In Column 10, Line 8, in Claim 12, delete "movable:" and insert --movable-- therefor Signed and Sealed this
Twenty-eighth Day of November, 2023

Katherine Kelly Vidal
*Director of the United States Patent and Trademark Office*